United States Patent
Murphy et al.

(10) Patent No.: US 11,053,282 B2
(45) Date of Patent: *Jul. 6, 2021

(54) PEPTOID AFFINITY LIGANDS

(71) Applicant: MIKE-ANN, LLC, Baton Rouge, LA (US)

(72) Inventors: Andrew J. Murphy, Cary, NC (US); Tee Bordelon, Holly Springs, NC (US); Michael Crapanzano, Baton Rouge, LA (US)

(73) Assignee: MIKE-ANN, LLC, Baton Rouge, LA (US)

( * ) Notice: Subject to any disclaimer, the term of this patent is extended or adjusted under 35 U.S.C. 154(b) by 15 days.

This patent is subject to a terminal disclaimer.

(21) Appl. No.: 16/083,366

(22) PCT Filed: Mar. 9, 2017

(86) PCT No.: PCT/US2017/021660
§ 371 (c)(1),
(2) Date: Sep. 7, 2018

(87) PCT Pub. No.: WO2017/156324
PCT Pub. Date: Sep. 14, 2017

(65) Prior Publication Data
US 2019/0085022 A1 Mar. 21, 2019

Related U.S. Application Data

(60) Provisional application No. 62/305,831, filed on Mar. 9, 2016, provisional application No. 62/305,835, filed on Mar. 9, 2016.

(51) Int. Cl.
*C07K 7/06* (2006.01)
*C07K 5/083* (2006.01)
(Continued)

(52) U.S. Cl.
CPC ............ *C07K 1/22* (2013.01); *B01D 15/3809* (2013.01); *B01J 20/265* (2013.01); *B01J 20/289* (2013.01);
(Continued)

(58) Field of Classification Search
CPC ... C07K 7/06; C07K 7/02; C07K 1/22; C07K 5/1008; C07K 5/1019; C07K 16/00;
(Continued)

(56) References Cited

U.S. PATENT DOCUMENTS 7,834,144 B2  11/2010  Peretz et al.
10,065,988 B2  9/2018  Menegatti
(Continued)

FOREIGN PATENT DOCUMENTS

EP  3426672 A   1/2019
EP  3426673 B1  5/2021
(Continued)

OTHER PUBLICATIONS

Fara et al. "Microwave-assisted coupling with DIC/HOBt for the synthesis of difficult peptoids and fluorescently labelled peptides—a gentle heat goes a long way," Tet. Lett., vol. 47, Iss. 6, pp. 1011-1014 (2006).
(Continued)

*Primary Examiner* — Shafiqul Haq
(74) *Attorney, Agent, or Firm* — Jenkins, Wilson, Taylor & Hunt, P.A.

(57) ABSTRACT

Disclosed herein are peptoids and related compounds, including peptoid affinity ligands, and hybrid peptoids, for binding and/or purifying immunoglobulins, immunoglobulin fragments or immunoglobulin fusion proteins thereof. Methods of making peptoid affinity ligands and using the same to bind, purify and/or isolate immunoglobulins and related compounds are also disclosed. Such peptoid affinity
(Continued)

ligands comprise a peptoid compound consisting of sequentially coupled peptoid residues forming a peptoid backbone, with one or more functional groups appended to a Nitrogen of the peptoid residues of the peptoid backbone configured to provide the desired binding affinity. The peptoids can further comprise a peptoid backbone with at least one functional group coupled to an alpha carbon (C) of a peptide bond in the peptoid backbone thereby forming a hybrid peptoid.

5 Claims, 5 Drawing Sheets

(51) Int. Cl.
| | |
|---|---|
| B01D 15/38 | (2006.01) |
| B01J 20/26 | (2006.01) |
| C07K 1/22 | (2006.01) |
| B01J 20/289 | (2006.01) |
| B01J 20/32 | (2006.01) |
| C07K 16/00 | (2006.01) |
| C07K 5/103 | (2006.01) |
| C07K 7/02 | (2006.01) |
| C07K 5/11 | (2006.01) |

(52) U.S. Cl.
CPC ....... *B01J 20/3204* (2013.01); *B01J 20/3208* (2013.01); *B01J 20/3212* (2013.01); *B01J 20/3219* (2013.01); *B01J 20/3274* (2013.01); *C07K 5/0806* (2013.01); *C07K 5/1008* (2013.01); *C07K 5/1019* (2013.01); *C07K 7/02* (2013.01); *C07K 7/06* (2013.01); *C07K 16/00* (2013.01); *B01J 2220/52* (2013.01)

(58) Field of Classification Search
CPC ............... C07K 5/0806; B01D 15/3809; B01J 20/3274; B01J 20/3212; B01J 20/289; B01J 20/3208; B01J 20/265; B01J 20/3204; B01J 20/3219; B01J 2220/52
See application file for complete search history.

(56) References Cited

U.S. PATENT DOCUMENTS

| | | | |
|---|---|---|---|
| 2003/0017508 A1 | 1/2003 | Charych et al. | |
| 2011/0092384 A1 | 4/2011 | Kwon et al. | |
| 2015/0377879 A1* | 12/2015 | Kodadek | G01N 33/564 506/9 |
| 2016/0075734 A1 | 3/2016 | Menegatti | |
| 2019/0337980 A1* | 11/2019 | Murphy | B01J 20/3204 |

FOREIGN PATENT DOCUMENTS

| | | |
|---|---|---|
| JP | H 11-507049 A | 6/1999 |
| JP | 2009-507833 A | 2/2009 |
| JP | 2012-527904 A | 11/2012 |
| JP | 2012-529053 A | 11/2012 |
| JP | 2014-504594 A | 2/2014 |
| JP | 2014-515739 A | 7/2014 |
| WO | WO 2009/134942 A1 | 11/2009 |
| WO | WO 2010/141421 A1 | 12/2010 |
| WO | WO 2012/096893 A2 | 7/2012 |
| WO | WO 2012/129423 A2 | 9/2012 |
| WO | WO 2013/043669 A1 | 3/2013 |
| WO | WO 2014/179714 A1 | 11/2014 |
| WO | WO 2014/194073 A1 | 12/2014 |
| WO | WO 2017/156319 | 9/2017 |

OTHER PUBLICATIONS

Gorske et al. "Local and Tunable n→π* Interactions Regulate Amide Isomerism in the Peptoid Backbone," J. Am. Chem. Soc., vol. 129, pp. 8928-8929 (2007).
Hara et al. "Probing the Structural Requirements of Peptoids That Inhibit HDM2-p53 Interactions," J. Am. Chem. Soc., vol. 128, pp. 1995-2004 (2006).
Haynes et al. "Comblike, Monodisperse Polypeptoid Drag-Tags for DNA Separations by End-Labeled Free-Solution Electrophoresis (ELFSE)," Bioconjugate Chem., vol. 16, pp. 929-938 (2005).
Kwon et al. "Quantitative Evaluation of the Relative Cell Permeability of Peptoids and Peptides," J. Am. Chem. Soc., vol. 129, pp. 1508-1509 (2007).
Miller et al. "Comparison of the Proteolytic Susceptibilities of Homologous L-Amino Acid, D-Amino Acid, and N-Substituted Glycine Peptide and Peptoid Oligomers," Drug Development Research, vol. 35, pp. 20-32 (1995).
Mora et al. "Identification from a Positional Scanning Peptoid Library of in Vivo Active Compounds That Neutralize Bacterial Endotoxins," J. Med. Chem., vol. 48, pp. 1265-1268 (2005).
Nam et al. "Free-floating ultrathin two-dimensional crystals from sequence-specific peptoid polymers," Nature Materials, vol. 9, pp. 454-460 (2010).
Nguyen et al. "Improving SH3 domain ligand selectivity using a non-natural scaffold," Chem. Biol., vol. 7, pp. 463-473 (2000).
Nielsen, P.E. ed., Pseudo-peptides in Drug Discovery, 1st ed., Wiley-VCH, pp. 1-31 (2004).
Olivos et al. "Microwave-Assisted Solid-Phase Synthesis of Peptoids," Org. Lett., vol. 4, No. 23, pp. 4057-4059 (2002).
Pakiman et al. "Comparison of Binding Capacity and Affinity of Monoclonal Antibody towards Different Affinity Resins using High-Throughput Chromatography Method," Journa of Applied Sciences, vol. 12, Iss. 11, pp. 1136-1141 (2012).
Park et al. "Structural and Dynamical Characteristics of Peptoid Oligomers with Achiral Aliphatic Side Chains studied by Molecular Dynamics Similation," author manuscript, pp. 1-24, 2012 [published in final edited form as: J. Phys. Chem. B., vol. 115, No. 37, pp. 10967-10975 (2011)].
Patch et al. "Helical Peptoid Mimics of Magainin-2 Amide," J. Am. Chem. Soc., vol. 125, pp. 12092-12093 (2003).
Peretto et al. "Cell penetrable peptoid carrier vehicles: synthesis and evaluation," Chem. Commun., pp. 2312-2313 (2003).
Pirrung et al. "19F-Encoded Combinatorial Libraries: Discovery of Selective Metal Binding and Catalytic Peptoids," J. Comb. Chem., vol. 4, pp. 329-344 (2002).
Sanborn et al. "Extreme stability of helices formed by water-soluble poly-N-substituted glycines (polypeptoids) with α-chiral side chains," Biopolymers, vol. 63, Iss. 1, pp. 1-32 (2002).
Schröder et al. "Peptoidic Amino- and Guanidinium-Carrier Systems: Targeted Drug Delivery into the Cell Cytosol or the Nucleus," J. Med. Chem., vol. 51, pp. 376-379 (2008).
Shah et al. "Oligo(N-aryl glycines): A New Twist on Structured Peptoids," J. Am. Chem Soc., vol. 130, pp. 16622-16632 (2008).
Statz et al. "Surface-immobilized antimicrobial peptoids," author manuscript, pp. 1-20, 2009b [Published in final edited form as: Biofouling, vol. 24, No. 6, pp. 439-448 (2008)].
Wu et al. "Helical Peptoid Mimics of Lung Surfactant Protein C," Chem. Biol., vol. 10, pp. 1057-1063 (2003).
Zuckermann et al. "Efficient Method for the Preparation of Peptoids [Oligo(N-substituted glycines)] by Submonomer Solid-Phase Synthesis," J. Am. Chem. Soc., vol. 114, pp. 10646-10647 (1992).
Office Action (Restriction Requirement) corresponding to U.S. Appl. No. 16/083,361 dated May 12, 2020.
International Preliminary Report on Patentability corresponding to International application No. PCT/US2017/021660 dated Sep. 11, 2018.
International Preliminary Report on Patentability corresponding to International application No. PCT/US2017/021655 dated Sep. 11, 2018.
Written Opinion of the International Searching Authority corresponding to International application No. PCT/US2017/021660 dated May 31, 2017.

(56) References Cited

OTHER PUBLICATIONS

Written Opinion of the International Searching Authority corresponding to International application No. PCT/US2017/021655 dated May 26, 2017.
International Search Report corresponding to International Application No. PCT/US2017/021660 dated May 31, 2017.
International Search Report corresponding to International Application No. PCT/US2017/021655 dated May 26, 2017.
Thakkar et al., "High-Throughput Sequencing of Peptoids and Peptide-Peptoid Hybrids by Partial edman Degration and Mass Spectrometry," Journal of Combinatorial Science, vol. 11, pp. 294-302 (2009).
Brown et al.,"Biomimicry of Surfactang ProteinC," Acc. Chem. Res. vol. 41, No. 10 pp. 1409-1417 (2008).
Chongsiriwatana et al.,"Peptoids that mimic the structure, function, and mechanism of helial antimicrobial peptides" PNAS, vol. 105, No. 8 pp. 2794-2799 (2008).
Drexler, K.E., "Peptoids at the 7th Summit: Toward Macromolecular Systems Engineering," Peptide Science, vol. 96, pp. 537-544 (2011).
Kirshenbaum et al.,"Sequence-specific polypeptoids: A diverse family of heteropolymers with stavle secoondary structure," PNAS, vol. 95 pp. 4303-4308 (1998).
Maayan et al., "Folded biomimetic oligomers for enantioselective catalysis," PNAS, vol. 106, pp. 13679-13684 (2009).
Murphy et al., "A combinatorial approach to the discovery of efficient cationic peptoid reagents for gene delivery," PNAS, vol. 95 pp. 1517-1522 (1998).
Reddy et al.,"Protein "fingerprinting" in complex mixtures with peptoid microarrays," Proc. Nat. Acad. Sci, USA, vol. 102, pp. 12672-12677 (2005).
Statz et al.,"Experimental and theoretical investigation of chain length and surface coverage on fouling of surface grafted polypeptoids," Biointerphases, vol. 4 FAA22-FA32 (2009).
Wender et al., Proc. Nat. Acad. Sci. USA vol. 97, pp. 13003-13008 (2000).
Zuckermann et al., J. Med. Chem. vol. 37 pp. 2678-2685 (1994).
Notice of Publication corresponding to European Application No. 17764138.8-1109 dated Dec. 19, 2018.
Notice of Publication corresponding to European Application No. 17764134.7-1109 dated Dec. 19, 2018.
Notice of Publication corresponding to U.S. Appl. No. 16/083,361 dated Nov. 8, 2019.
European Search Report corresponding to European Application No. 17764138 dated Sep. 5, 2019.
European Search Report corresponding to European Application No. 17764134 dated Oct. 7, 2019.
Kruijtzer et al., "Peptoid-Peptide Hybrids as Potent Novel Melanocortin Recepter Ligands," Journal of Medicinal Chemistry, vol. 48, No. 13, pp. 4224-4230 (2005).
Reddy et al., "Identification of Candidate IgG Biomarkers for Alzheimer's Disease via Combinatorial Library Screening," Cell, vol. 144, No. 1, pp. 132-142 (2011).
Ryge et al., "Potent antibacterial lysine-peptoid hybrids identified from a positional scanning combinatorial library," Bioorganic & Medicinal Chemistry: A Tetrahedron Publication for the Rapid Dissemination of Full Original Research Papers and Critical Reviews on Biomolecular Chemistry, Medicinal Chemistry and Related Disciplines, vol. 14, No. 13, pp. 4444-4451 (2006).
Liu et al., "A Potent Transactivation Domain Mimic with Activity in Living Cells," Journal of the American Chemical Society, vol. 127, No. 23 pp. 8254-8255 (2005).
Doran et al., "Discovery of Native Autoantigens via Antigen Surrogate Technology: Application to Type 1 Diabetes," ACS Chemical Biology, vol. 10, No. 2 pp. 401-412 (2014).
Prasanna et al., "Isolation of protein ligands from large peptoid libraries," Journal of the American Chemical Society, American Chemical Society, vol. 125, No. 46 pp. 13995-14004 (2003).
Office Action corresponding to U.S. Appl. No. 16/083,361 dated Oct. 14, 2020.
Office Action corresponding to European Application Serial No. 177641347-1109 dated Sep. 4, 2020.
Alluri et al. "Isolation and characterization of coactivator-binding peptoids from a combinatorial library," Molecular Biosystems, vol. 2, No. 11, pp. 568-579 (2006).
Intent to Grant corresponding with European Patent Application No. 17764138.8-1109 dated Nov. 25, 2020.
Office Action corresponding to Japanese Patent Application No. 2018-567015 dated Dec. 7, 2020.
Office Action corresponding to Japanese Patent Application No. 2018-567016 dated Dec. 22, 2020 [Machine translation].
Simpson et al. "A cleavable scaffold strategy for the synthesis of one-bead one-compound cyclic peptoid libraries that can be sequenced by tandem mass spectrometry," Tetrahedron Letters, vol. 53, Iss. 18, pp. 2341-2344 (2012).
Doran et al. "Discovery of Native Autoantigens via Antigen Surrogate Technology: Application to Type 1 Diabetes," Acs Chemical Biology, vol. 10, No. 2 pp. 401-412 (2015).
Pels et al. "Solid-Phase Synthesis of Diverse Peptide Tertiary Amides by Reductive Amination," ACS Combinatorial Science, vol. 17, No. 3, pp. 152-155 (2015).
Grant Decision corresponding to European Patent Application No. 17764138.8-1109 dated Apr. 9, 2021.
Intent to Grant corresponding to European Patent Application No. 17764134.7—1109 dated May 7, 2021.

\* cited by examiner

PEPTOID AFFINITY LIGANDS

CROSS REFERENCE TO RELATED APPLICATIONS

This application claims the benefit of and priority to U.S. Provisional Patent Application Ser. No. 62/305,831, filed Mar. 9, 2016, and U.S. Provisional Patent Application Ser. No. 62/305,835, filed Mar. 9, 2016, the disclosures of which are incorporated herein by reference in their entireties.

TECHNICAL FIELD

Disclosed herein are peptoids and related compounds, including peptoid affinity ligands. Methods of making peptoid affinity ligands and using the same to bind purify and/or isolate immunoglobulins and related compounds are also disclosed.

BACKGROUND

Monoclonal antibodies and Fc-fusion proteins have emerged as an important class of therapeutic proteins for the treatment of a number of unmet diseases such as cancer, autoimmune diseases, immunodeficiency, skin disorders and neurological disorders. These products account for 40% of the overall pharmaceutical market with a volume of $35 billion in 2011.

However, therapies based on antibodies are very expensive to consumers. Their high price is due in part to the high cost of isolation and purification of these biomolecules. A major contribution to the purification costs results from the ubiquitous use of Protein A or Protein G affinity chromatography to in the capture step. Despite their high selectivity for IgG, these protein ligands suffer from high cost and low chemical and biochemical stability. The average cost of Protein A/G-based chromatographic media ranges between about $8,000 to about $15,000 per liter of resin. Moreover, protein ligands show in general poor chemical resistance towards the alkaline (0.1-1.0 M NaOH) cleaning-in-place and sanitization-in-place procedures periodically applied for the removal of contaminants, and required by regulatory guidelines. Further, they are prone to proteolytic degradation by enzymes present in the feed. Both chemical and enzymatic agents can cause ligand degradation and leakage of ligand fragments from the resin, resulting in shorter column lifetime and potential presence of toxic and immunogenic leachates in the product mainstream.

What is needed are inexpensive and robust ligands with high affinity and selectivity for antibodies. Improved ligands capable of effectively isolating and purifying antibodies, Fc-fusion and related therapeutic proteins could make immunotherapies more cost effective.

SUMMARY

Provided herein are affinity ligands generally characterized as peptoids. Peptoids possesses ideal characteristics for affinity purification applications.

First, the display of functional groups on peptoids in some embodiments resembles that of peptides, implying that peptoids can be designed or selected with levels of affinity and selectivity comparable to those of peptide ligands. Further, owing to the so-called "sub-monomer" protocol of synthesis, which employs primary amines, peptoids can explore a much wider chemical diversity than that available to protein ligands and peptides comprising natural amino acids. Disclosed herein is the understanding of the ability to fine tune their composition to achieve higher target specificity and affinity. Finally, peptoids are completely resistant to proteolysis and are therefore advantageous for the purification of antibodies from fluids containing active enzymes, like whole plasma and its fractions or lysates of cell cultures, plants and other organisms. Peptoids are therefore an economical alternative to Protein A. Besides the purification of biopharmaceuticals, these ligands can find further applications in areas such as diagnostics and process control.

Accordingly, a first aspect of the invention is a peptoid ligand that specifically binds to an antibody such as IgG, and/or an antibody Fc fragment, and/or an Fc-fusion protein. Such peptoid ligands are in some embodiments from 3 to 9 residues or monomers in length. Such peptoid ligands are optionally, but in some embodiments preferably, coupled to a solid support.

Thus, provided herein are peptoid affinity ligands comprising a peptoid compound consisting of sequentially coupled peptoid residues forming a peptoid backbone, with one or more functional groups appended to a Nitrogen of the peptoid residues of the peptoid backbone, wherein the one or more functional groups comprise, in any order but coupled to sequential peptoid residues on the peptoid backbone: at least two aromatic functional groups and either a basic or acidic functional group, subject to the proviso that excluded therefrom are peptoid affinity ligands containing a contiguous segment of three peptoid residues with the following functional groups: (i) a basic residue, (ii) an aromatic residue, and (iii) a basic residue or hydrophilic residue.

Also provided are peptoid affinity ligands comprising a peptoid compound consisting of sequentially coupled peptoid residues forming a peptoid backbone, with one or more functional groups appended to a Nitrogen of the peptoid residues of the peptoid backbone, wherein the one or more functional groups include at least two aromatic functional groups and at least one basic or acidic functional group, subject to the proviso that excluded therefrom are peptoid affinity ligands containing, from a N-terminus to a C-terminus of the peptoid backbone, a contiguous segment of three peptoid residues with the following functional groups: (i) a basic residue, (ii) an aromatic residue, and (iii) a basic residue or hydrophilic residue.

Such peptoid compounds as disclosed herein can also be subject to the proviso that excluded therefrom are peptoid affinity ligands containing, from a N-terminus to a C-terminus, and at the N-terminus position, of the peptoid backbone, a contiguous segment of three peptoid residues with the following functional groups: (i) a basic residue, (ii) an aromatic residue, and (iii) a basic residue or hydrophilic residue.

The peptoids and affinity ligands also specifically bind an immunoglobulin, c wherein the immunoglobulin, immunoglobulin fragment or immunoglobulin fusion protein thereof is one or more of IgG, IgA, IgE, IgD, IgM or IgY.

A further aspect of the invention is a method of binding an antibody, or antibody Fc fragment, or an Fc-fusion protein from a liquid composition containing the same, comprising the steps of: (a) providing a solid support comprising a peptoid ligand bound thereto as described herein, (b) contacting said composition to said solid support so that antibody or Fc fragments bind to said compound; and (c) separating said liquid composition from said solid support, with said antibody or Fc fragment bound to said solid support. Such methods can also comprise (d) elution or separation of bound antibodies and/or immunoglobulins from compound/solid support.

The foregoing and other objects and aspects of the present disclosure are explained in detail in the specification set forth below.

Embodiments of the presently disclosed subject matter having been stated hereinabove, and which is achieved in whole or in part by the presently disclosed subject matter, other embodiments will become evident as the description proceeds when taken in combination with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which.

DETAILED DESCRIPTION

Figure 1:
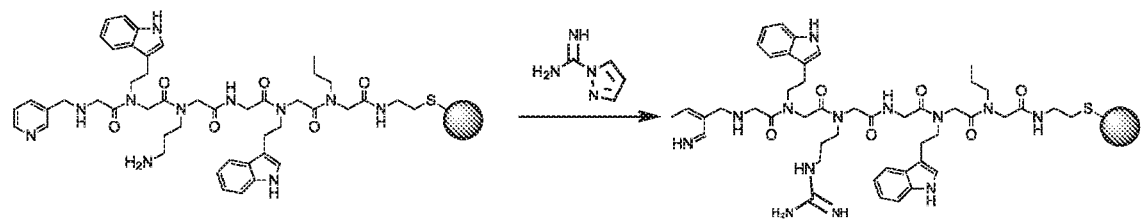
FIG. 1 is a schematic illustration of the conversion of peptoid primary amine to guanidinyl group on a chromatographic support.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a tool" includes a plurality of such tools, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

"Peptoid" as used herein refers to poly-N substituted glycines with one or more functional groups, and/or functional residues. Peptoids and peptoid compounds as disclosed herein can comprise sequentially coupled peptoid residues forming a peptoid backbone, with one or more functional groups appended to a Nitrogen (N) of the peptoid residues of the peptoid backbone, and not an alpha carbon (C). As disclosed herein, the term "peptoid", "peptoid compounds", and/or "peptoid affinity ligand" can be used interchangeably.

"Functional group", or "functional residue", as used herein may be any suitable group or substituent, including but not limited to H, linear and cyclic alkyl, alkenyl, and alkynyl, possibly substituted and/or functionalized with groups such as alkoxy, halo, mercapto, azido, cyano, formyl, carboxyl, hydroxyl, nitro, acyl, aryloxy, alkylthio, amino, alkylamino, arylalkylamino, substituted amino, acylamino, acyloxy, ester, thioester, carboxylic thioester, ether, amide, amidino, sulfate, sulfoxyl, sulfonyl, sulfonyl, sulfonic acid, sulfonamide, urea, alkoxylacylamino, aminoacyloxy, guanidino, aldehyde, keto, imine, nitrile, phosphate, thiol, epoxide, peroxide, thiocyanate, amidine, oxime, nitrile, diazo, etc., these terms including combinations of these groups (e.g. alkylated groups) as discussed further below.

"Heterocyclic" as used herein alone or as part of another group refers to a cyclic compound that has atoms of at least two different elements as members of its ring(s).

"Alkyl" as used herein alone or as part of another group, refers to a straight, branched chain, or cyclic, saturated or unsaturated, hydrocarbon containing from 1 or 2 to 10 or 20 carbon atoms, or more. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Alkyl may be saturated or unsaturated and hence the term "alkyl" as used herein is inclusive of alkenyl and alkynyl when the alkyl substituent contains one or more unsaturated bond (for example, one or two double or triple bonds). The alkyl group may optionally contain one or more heteroatoms (e.g., one, two, or three or more heteroatoms independently selected from O, S, and NR', where R' is any suitable substituent such as described immediately above for alkyl substituents), to form a linear heteroalkyl or heterocyclic group as specifically described below.

"Alkenyl" as used herein refers to an alkyl group as described above containing at least one double bond between two carbon atoms therein.

"Alkynyl" as used herein refers to an alkyl group as described above containing at least one triple bond between two carbon atoms therein.

"Alkylene" as used herein refers to an alkyl group as described above, with one terminal hydrogen removed to form a bivalent substituent.

"Aromatic" as used herein alone or as part of another group refers to group containing a planar unsaturated ring of atoms that is stabilized by an interaction of the bonds forming the ring. Such compounds can in some instances be typified by benzene and its derivatives. An aromatic functional group or other substituent can also be called an aryl group.

"Heteroaromatic" as used herein alone or as part of another group refers to having the characteristics of an aromatic compound or aryl group whilst having at least one non-carbon atom in the ring.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical or a —N(R$_a$)C(O)R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Solid support" as used herein may comprise any suitable material, including organic materials (e.g., organic polymers), metals (e.g., titanium), inorganic materials (e.g., silica) and composites thereof. The solid supports may be in any suitable shape or form, including membrane fibers and films (regenerated cellulose), receptacles such as microtiter plate wells (e.g., floors and/or walls thereof) particles (e.g., resins or beads formed from natural or synthetic polymers, inorganic materials such as glass or silica, composites thereof, etc.) such as for chromatography column packings, etc.

"Coupling group" as used herein may be any suitable reactive group, e.g., an alkene, alkyne, alcohol, thiol, selenyl, phosphono, carboxylic acid, formyl, halide or amine group, displayed directly by the parent molecule or by means of an intervening linker group (e.g., an aliphatic, aromatic, or mixed aliphatic/aromatic group such as an alkyl, aryl, arylalkyl, or alkylarylalkyl group, etc.).

Disclosed herein are peptoid affinity ligands configured to specifically bind immunoglobulins, immunoglobulin fragments and/or immunoglobulin fusion proteins thereof. By way of example and not limitation, the peptoids disclosed herein can in some embodiments be used to bind to, collect, purify, immobilize on a solid surface, etc., any type of antibody or antibody fragment (e.g., Fc fragments, Fab fragments, and scFV fragments), including both natural and recombinant (including chimeric) antibodies, engineered multibodies, single domain antibodies, and combinations thereof, such as divalent antibodies and camelid immunoglobulins, and both monoclonal and polyclonal antibodies, or an Fc-fusion protein. The antibodies may be of any species of origin, or from any subject, including mammalian (rabbit, mouse, rat, cow, goat, sheep, llama, camel, alpaca, etc), avian (e.g., chicken, duck, turkey, etc.), chondrichthyes (shark IgNAR, etc.), including fragments, chimeras and combinations thereof as noted above.

The term "subject" as used herein refers to a member of any invertebrate or vertebrate species. Accordingly, the term "subject" is intended to encompass any member of the Kingdom Animalia including, but not limited to the phylum Chordata (e.g., members of Classes Osteichythyes (bony fish), Amphibia (amphibians), Reptilia (reptiles), Aves (birds), and Mammalia (mammals)), and all Orders and Families encompassed therein. By way of example and not limitation, such subject can include humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Such subjects can also include birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans.

The antibodies may be of any type of immunoglobulin, including but not limited to IgG, IgA, IgE, IgD, IgM, IgY (avian), etc. The antibodies may be of any isotypes, e.g. IgA1, IgA2, IgG1, IgG2, IgG3, IgG4, etc., or other subclass, and of any other species, e.g. rat, mouse, goat, llama, etc.

In some embodiments, the antibodies or Fc fragments (including fusion proteins thereof) are carried in a biological fluid such as blood or a blood fraction (e.g., blood sera, blood plasma), egg yolk and/or albumin, tissue or cell growth media, a tissue lysate or homogenate, etc.

The disclosed peptoid affinity ligands, or peptoids, can in some aspects comprise compounds of Formulas I to V:

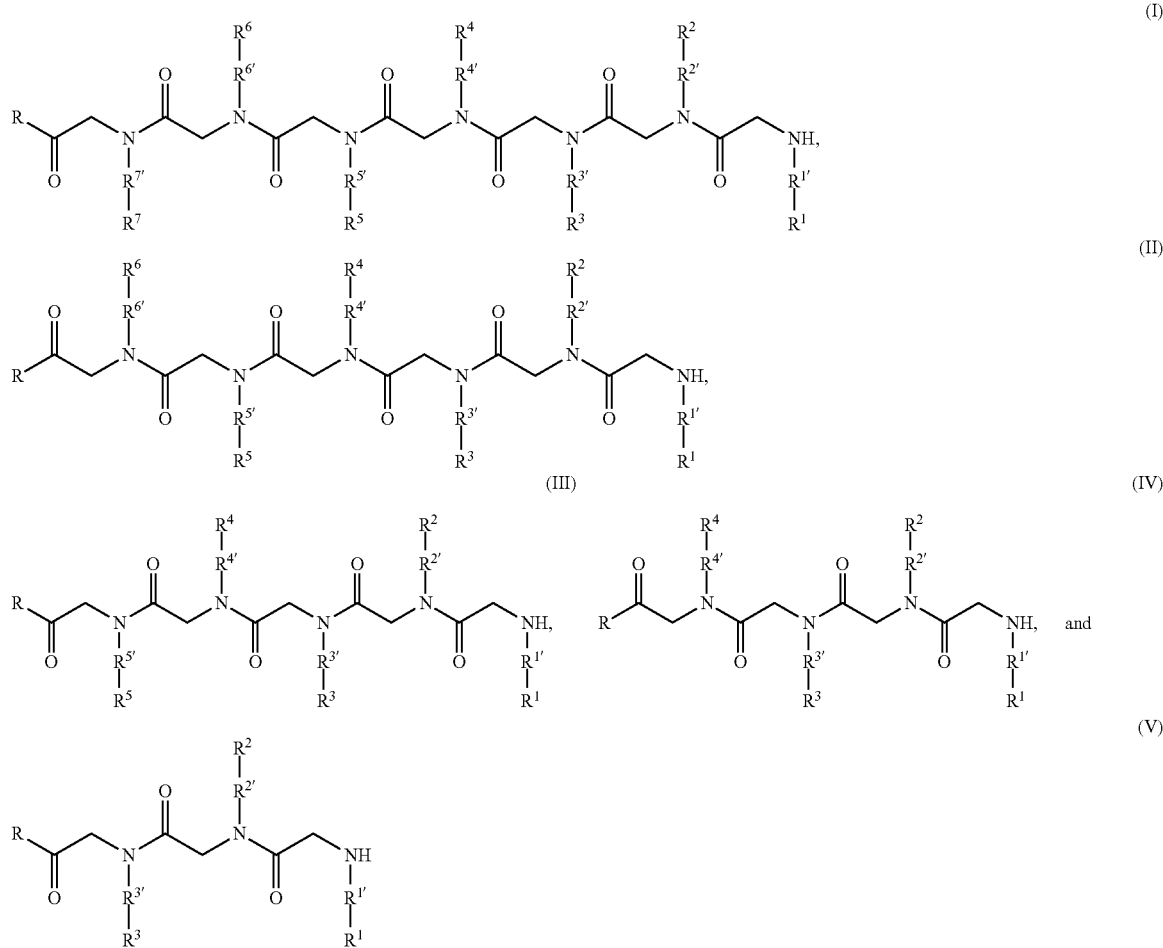

wherein:
R is a linking moiety (e.g., R is —OH, —NH$_2$, —NHR", —OR", —O—O—R", etc., where R" is alkyl, etc.) or —Z—R', where Z is a linking group and R' is a solid support (e.g., Z is —O—, —NH—, —O—NH—, —O—R"—S—, —NH—R"—S—, —O—NH—R"—S—, —O—R"—S—S—, —NH—R"—S—S—, —O—NH—R"—S—S—; ether (—O—), thioether (—S—), thioester, carbamate, carbonate, amide, ester, secondary/tertiary amine (e.g., obtained through a reductive amination coupling reaction), alkyl (e.g., obtained through a metathesis coupling reaction), alkenyl, phosphodiester, phosphoether, oxime, imine, hydrazone, acetal, hemiacetal, semicarbazone, ketone, ketene, aminal, hemiaminal, enamine, enol, disulphide, sulfone, cysteamide, cysteine, lysine, 2-azidoglycine, 2-alkynylglycine, etc.);

$R^{1'}$, $R^{2'}$, $R^{3'}$, $R^{4'}$, $R^{5'}$, $R^{6'}$, and $R^{7'}$ are each independently absent or a C1 to C4 alkylene group;

$R^1$, $R^2$, $R^3$, $R^4$, $R^5$, $R^6$, and $R^7$ are each independently as described herein and include one or more functional groups or functional residues oriented in any order as described herein such that the resulting peptoid has binding affinity to one or more immunoglobulins as described herein.

In some embodiments such peptoid affinity ligands can comprise a peptoid compound consisting of sequentially coupled peptoid residues forming a peptoid backbone, e.g. as shown in Formulas I-V, with one or more functional groups appended to a Nitrogen of the peptoid residues of the peptoid backbone, e.g. $R^1$, $R^2$, $R^3$, $R^4$, $R^5$, $R^6$, and $R^7$ as shown in Formulas I-V. In some aspects the peptoid backbone can be cyclized.

In some embodiments herein the peptoid compounds and peptoid affinity ligands comprise a peptoid backbone with at least one alpha carbon (C) functional group, i.e. a true peptide bond with the functional group coupled to the C instead of the nitrogen (N) in the peptoid. That is, amongst the sequentially coupled peptoid residues forming the peptoid backbone there is at least one functional group coupled to an alpha carbon of a peptide bond in the peptoid backbone. In some embodiments, one or more, or a plurality, of functional groups, as described herein, can be coupled to one or more alpha carbons of the backbone to form a peptoid-like or peptide-like compound that acts as a hybrid between a pure peptoid (all functional groups attached to nitrogen on the backbone) and a pure peptide (all functional groups attached to carbon on the backbone). In some embodiments these hybrid structures can be mostly or substantially peptoid or peptoid-like, i.e. substantially all peptoid residues, whereas in some embodiments such hybrid structures can be mostly or substantially peptide or peptide-like, i.e. substantially all peptide residues. In some embodiments a hybrid peptoid can be about 50% peptoid residues and 50% peptide residues. In Table 2 below the functional group attached to an alpha carbon within the peptoid backbone is indicated by a star.

The functional groups, or R-groups, can comprise any side chain, amine, chemical structure, etc., exemplified herein, but not necessarily limited to those examples disclosed, discussed or shown herein. By way of example and not limitation, Table 1 provides exemplary R-groups, or functional groups for the disclosed peptoids and peptoid affinity ligands.

TABLE 1

| Residue ID | Residue Classification | R' | R | Structure |
|---|---|---|---|---|
| $P_3$ | Aromatic | —CH$_2$— | 3-pyridyl | 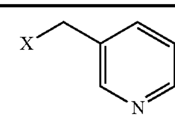 |
| W | Aromatic | —CH$_2$CH$_2$— | 3-indole | 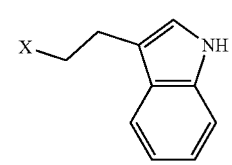 |
| R | Basic | —CH$_2$CH$_2$CH$_2$— | —NH(CNH)NH$_2$ | 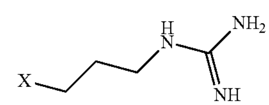 |
| U | Basic | —CH$_2$CH$_2$CH$_2$— | —NH(CO)NH$_2$ | 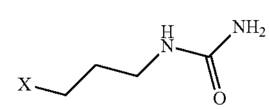 |
| G | Non-Polar | H | N/A | X—H |
| $P_5$ | Basic | —CH$_2$CH$_2$CH$_2$— | —NH$_2$ | 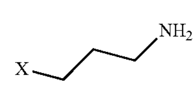 |
| $P_n$ | Aliphatic | —CH$_2$CH$_2$CH$_3$ | N/A | 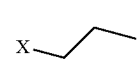 |
| S | Aliphatic | —CH$_3$ | N/A | 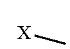 |
| $M_0$ | Polar | —CH$_2$CH$_2$— | —OCH$_3$ | 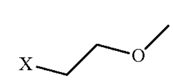 |

TABLE 1-continued

| Residue ID | Residue Classification | R' | R | Structure |
|---|---|---|---|---|
| D | Acidic | —CH$_2$CH$_2$— | —CO$_2$H | 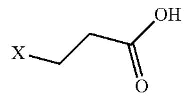 |
| M$_S$ | Non-Polar | —CH$_2$CH$_2$— | —SCH$_3$ | 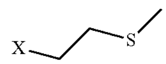 |
| Z | Aromatic | —CH$_2$— | —C$_6$H$_6$ | 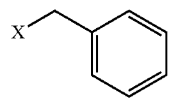 |
| Y | Aromatic | —CH$_2$CH$_2$ | -4-HOC$_6$H$_6$ | 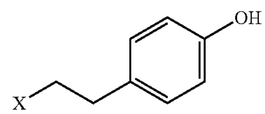 |
| K | Basic | —CH$_2$CH$_2$CH$_2$CH2— | —NH$_2$ | 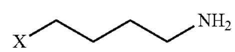 |
| J | Basic | —CH$_2$CH$_2$— | —NCH$_2$CH$_2$NHCO | 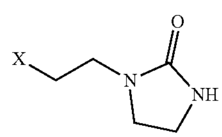 |
| R2 | Basic | —CH$_2$CH$_2$CH$_2$CH$_2$— | —NH(CNH)NH$_2$ | 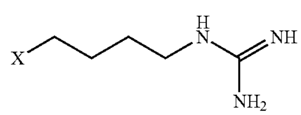 |
| E | Polar | —CH$_2$CH$_2$— | —OH | 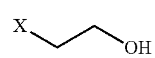 |
| H | Basic | —CH$_2$— | —CNCHNHCH— | 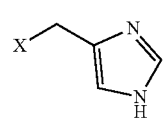 |

In some embodiments the one or more functional groups comprise, in any order but coupled to sequential peptoid residues on the peptoid backbone, at least two aromatic functional groups and either a basic or acidic functional group. Such functional groups, e.g. at least two aromatic functional groups and either a basic or acidic functional group, can be oriented in any way, or scrambled, so long as they are coupled to sequential peptoid residues and the peptoid specifically binds an immunoglobulin, immunoglobulin fragment or immunoglobulin fusion protein thereof, wherein the immunoglobulin, immunoglobulin fragment or immunoglobulin fusion protein thereof is one or more of IgG, IgA, IgE, IgD, IgM or IgY. In some aspects, an aromatic functional group comprises a heteroaromatic functional group.

By way of example and not limitation, such peptoids and peptoid affinity ligands can comprise one or more of the sequences and structures listed and shown below in Table 2.

TABLE 2

| Ligand ID | Ligand Structure | $K_d \times 10^{-6}$ | Qmax (mg/mL) |
|---|---|---|---|
| 16-81-4 | | 2.9 | 64 |
| 12-65-8 | | 3.6 | 57. |
| 12-65-5 | | 3.6 | 64 |

TABLE 2-continued

| Ligand ID | Ligand Structure | $K_d \times 10^{-6}$ | Qmax (mg/mL) |
|---|---|---|---|
| 16-83-6 | | 4.6 | 56 |
| 16-84-3 | | 4.9 | 56 |
| 16-83-9 | | 4.9 | 52 |

TABLE 2-continued

| Ligand ID | Ligand Structure | $K_d \times 10^{-6}$ | Qmax (mg/mL) |
|---|---|---|---|
| 16-83-2 | | 5.3 | 49 |
| 16-84-2 | | 6.5 | 48 |
| 16-83-5 | | 6.5 | 62 |

TABLE 2-continued
| Ligand ID | Ligand Structure | $K_d \times 10^{-6}$ | Qmax (mg/mL) |
|---|---|---|---|
| 16-83-3 | 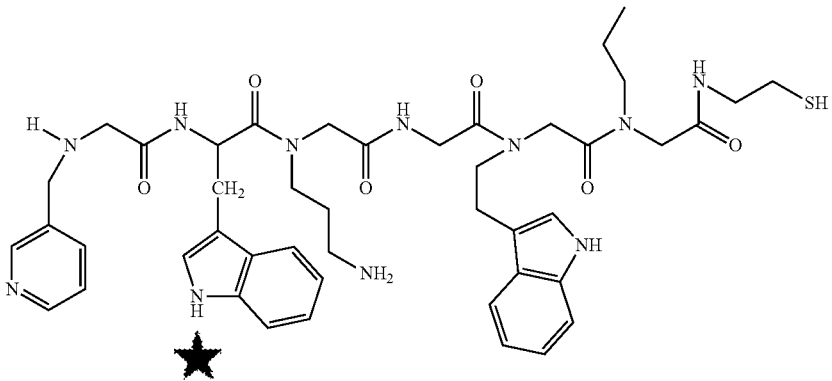 [SMILES: CCCN(CC(=O)NCCS)C(=O)CN(CCc1c[nH]c2ccccc12)C(=O)CNC(=O)CN(CCCN)C(=O)C(Cc1c[nH]c2ccccc12)NC(=O)CNCc1cccnc1] | 7.3 | 51 |
| 16-83-7 | 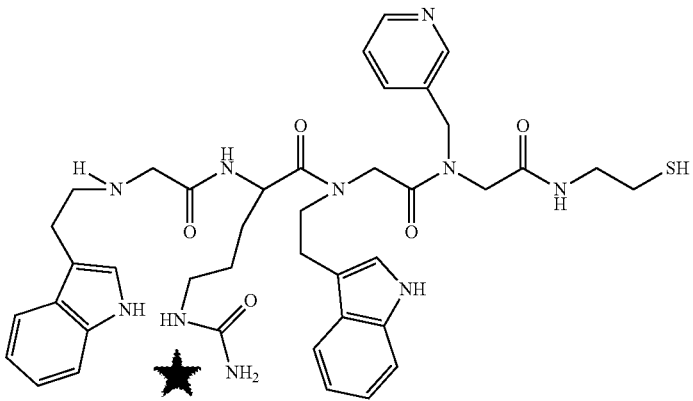 [SMILES: NC(=O)NCCCC(NC(=O)CNCCc1c[nH]c2ccccc12)C(=O)N(CCc1c[nH]c2ccccc12)CC(=O)N(CC(=O)NCCS)Cc1cccnc1] | 7.7 | 53 |
| 12-65-1 | 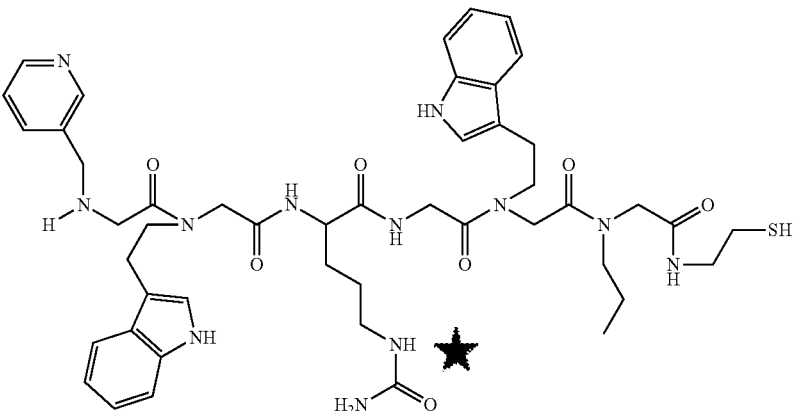 | 7.9 | 65 |
| 12-65-2 | 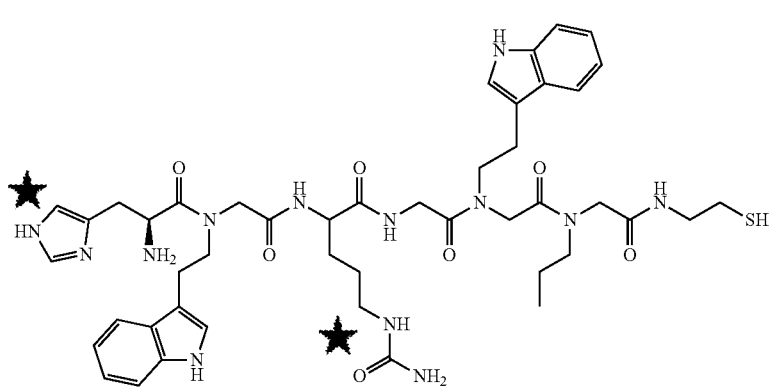 [SMILES: CCCN(CC(=O)NCCS)C(=O)CN(CCc1c[nH]c2ccccc12)C(=O)CNC(=O)C(CCCNC(N)=O)NC(=O)CN(CCc1c[nH]c2ccccc12)C(=O)[C@@H](N)Cc1c[nH]cn1] | 15 | 53 |

TABLE 2-continued

| Ligand ID | Ligand Structure | $K_d \times 10^{-6}$ | Qmax (mg/mL) |
|---|---|---|---|
| 12-55-6 | | 33 | 97 |
| 18-59 | | N/A | N/A |
| PV-19-1B | | N/A | N/A |

In some embodiments the one or more functional groups comprise at least two aromatic functional groups and either a basic or acidic functional group, positioned or appended to any Nitrogen of the peptoid residues of the peptoid backbone, and in any order. Such functional groups, e.g. at least two aromatic functional groups and either a basic or acidic functional group, can be oriented in any way, or scrambled, so long as the peptoid specifically binds an immunoglobulin, immunoglobulin fragment or immunoglobulin fusion protein thereof, wherein the immunoglobulin, immunoglobulin fragment or immunoglobulin fusion protein thereof is one or more of IgG, IgA, IgE, IgD, IgM or IgY. In some aspects, an aromatic functional group comprises a heteroaromatic functional group.

In some embodiments the disclosed peptoids and peptoid affinity ligands, whether requiring a specific sequence of functional groups or completely random/scattered, do not include peptoid affinity ligands containing a contiguous segment of three peptoid residues with the following functional groups: (i) a basic residue, (ii) an aromatic residue, and (iii) a basic residue or hydrophilic residue. In some aspects, excluded from the disclosed peptoids are those containing, from a N-terminus to a C-terminus, and at the N-terminus position, of the peptoid backbone, a contiguous segment of three peptoid residues with the following functional groups: (i) a basic residue, (ii) an aromatic residue, and (iii) a basic residue or hydrophilic residue.

In some embodiments the functional groups comprise non-natural amino acid functional groups, including D-amino acids and beta amino acids.

In some embodiments, peptoids and peptoid affinity ligands disclosed herein can comprise sequentially coupled peptoid residues forming a peptoid backbone comprising between 3 and 15 or more peptoid residues, including for example between 3 and 10 peptoid residues, between 3 and 9 peptoid residues, between 3 and 8 peptoid residues, between 3 and 7 peptoid residues, and so on.

The peptoid affinity ligands disclosed herein have been configured to have high binding affinities for immunoglobulins, and can therefore serve as effective and efficient purification ligands. By way of example and not limitation, the disclosed peptoid affinity ligands can have an equilibrium dissociation constant ($K_d$) for immunoglobulins, immunoglobulin fragments or immunoglobulin fusion proteins thereof of about $0.05 \times 10^{-6}$ molar to about $50 \times 10^{-6}$ molar, including for example about $0.5 \times 10^{-6}$ molar to about $10 \times 10^{-6}$ molar, about $0.5 \times 10^{-6}$ molar to about $5 \times 10^{-6}$ molar, and about $0.5 \times 10^{-6}$ molar to about $1 \times 10^{-6}$ molar.

In some embodiments the disclosed peptoid affinity ligands can be configured to bind and subsequently release a bound immunoglobulin, immunoglobulin fragment or immunoglobulin fusion protein thereof at a higher pH (i.e. less acidic) than might be required for other affinity ligands, e.g. protein-based ligands. For example, bound immunoglobulins or other target antigens can be released at a pH of about 3 to about 7, including for example a pH of about 4 to about 6, about 4 to about 5, about 3 to about 5 or about 4 to about 7. Such ligands that allow release of the bound immunoglobulin at a higher, or less acidic and more neutral, pH can in some aspects increase the stability and/or reusability of the ligand. Moreover, another benefit is imparted to the eluted immunoglobulin under these less acidic conditions. Particularly, the milder pH increases the stability of the eluted immunoglobulin, particularly for pH sensitive immunoglobulins, and in some embodiments even more advantageous for monoclonal antibodies, since they are in theory a population of homogeneous immunoglobulins.

An aspect of the presently disclosed peptoids and peptoid affinity ligands is their ability to not only bind immunoglobulins with high affinity and specificity, but do so while resisting degradation or denaturation of the peptoid itself. As such, in some embodiments the disclosed peptoids and related affinity ligands can be at least 50% or more resistant to proteolysis than protein-based ligands that bind immunoglobulins. In some embodiments they can be about 10%, 20%, 30%, 40%, 50% or more, and ranges thereof, resistant to proteolysis than protein-based ligands that bind immunoglobulins, e.g. protein A or G. Based on this robust characteristic and resistance to proteolysis the disclosed peptoids and peptoid affinity ligands can be suitable for multiple purification cycles, i.e. repetitive use. As such, the ligands disclosed herein can provide an advantage in efficiency and cost effectiveness over existing ligands.

In some embodiments the disclosed peptoids and peptoid affinity ligands are configured to effectively and efficiently bind IgM, in some embodiments at a substantially higher affinity than existing ligands and binding compounds. For example, the disclosed peptoid affinity ligands can have a $K_d$ for IgM of about $0.05 \times 10^{-6}$ to about $50 \times 10^{-6}$ molar, including for example about $0.5 \times 10^{-6}$ molar to about $10 \times 10^{-6}$ molar, about $0.5 \times 10^{-6}$ molar to about $5 \times 10^{-6}$ molar, and about $0.5 \times 10^{-6}$ molar to about $1 \times 10^{-6}$ molar.

The immunoglobulins, immunoglobulin fragments and/or immunoglobulin fusion proteins that can be bound, isolated or otherwise purified using the disclosed peptoids can include immunoglobulins and the like from any organism, including for example a mammal, an avian, a chondrichthyes, etc.

In some aspects the peptoid affinity ligands disclosed herein can be coupled to a solid support, including for example but not limited to a particle, an inorganic material, and/or an organic polymer material. In some embodiments such a solid support can comprise membrane fibers or films, including for example regenerated cellulose. Such solid supports can be useful in various applications such as membrane chromatography.

In some embodiments the solid support comprises a particle (e.g., a bead, such as a porous polymer bead like a pearl of chromatographic resin). In some embodiments the solid support comprises an inorganic material (e.g., silica, titania, zirconia, and the like). In some embodiments, the solid support comprises an organic polymer material (e.g., polyethersulfone, PMMA, etc.).

In some embodiments, the peptoid affinity ligand can be coupled to the solid support by a linkage other than a thiol linkage, preferably an amino linkage. By providing a peptoid with a linkage other than a thiol linkage the peptoid can in some embodiments have a binding affinity to an immunoglobulin, immunoglobulin fragment or immunoglobulin fusion protein thereof that is at least about 10% to about 20% better than a peptoid affinity ligand with a thiol linkage. Without being bound by any particularly theory or mechanism of action, such a linkage can allow one or more functional groups to orient or be positioned in a manner that optimizes and/or enhances binding affinity to one or more immunoglobulins.

In some embodiments, example peptoids as disclosed herein are also provided in Table 3 below. Such peptoids include between three and nine peptoid residues on a peptoid backbone, with corresponding functional groups or residues, R1 up through R9, shown in Table 3. The functional groups R1 through R9 for each correspond to the coding or residue IDs in Table 1 above.

TABLE 3

| Resin ID | R1 | R2 | R3 | R4 | R5 | R6 |
|---|---|---|---|---|---|---|
| 16-81-2 | P3 | W | * R | G | W | Pn |
| 12-80-4 | P3 | W | * U | W | | |
| 12-60-1 | P3 | W | * U | G | W | Pn |
| 16-81-4 | P3 | W | * U | W | | |
| 12-65-8 | P3 | Z | * U | * U | P3 | |
| 12-65-5 | * U | P3 | W | G | W | |
| 16-81-3 | P3 | W | * U | G | W | Pn |
| 18-59 | Mo | W | W | * U | | |
| 16-83-1 | P3 | W | * Ms | W | | |
| 12-65-7 | P3 | Z | * U | * U | | |
| 16-83-6 | P3 | W | P5 | G | W | * V |
| 16-84-3 | * U | P3 | W | P3 | | |
| 16-83-9 | * U | W | P3 | W | | |
| 16-83-2 | P3 | W | P5 | G | * W | Pn |
| 18-36-H | * W | G | W | Pn | | |
| 18-36-G | * W | G | W | Pn | | |
| 16-84-2 | P3 | W | * U | * U | | |
| 16-83-5 | * H | W | P5 | G | W | Pn |
| 16-83-4 | P3 | * W | P5 | G | W | Pn |
| 18-36-K | * U | W | P3 | | | |
| 18-36-A | P3 | W | * W | Pn | | |
| PV-19-1B | P3 | W | * U | W | | |

TABLE 3-continued

| Resin ID | R1 | R2 | R3 | R4 | R5 | R6 |
|---|---|---|---|---|---|---|
| 16-83-3 | P3 | *W | P5 | G | W | Pn |
| 16-83-7 | W | *U | W | P3 | | |
| 18-36-D | P3 | W | P5 | G | W | *V |
| 12-65-1 | P3 | W | *U | G | W | Pn |
| 12-55-4 | *U | P3 | W | G | W | |
| 12-60-2 | *H | W | *U | G | W | Pn |
| 18-36-B | *H | W | G | W | Pn | |
| 18-36-F | P3 | W | G | *V | | |
| 12-65-2 | *H | W | *U | G | W | Pn |
| 12-55-6 | P3 | Z | *U | *U | | |
| PV-9-96E | *U | Z | P3 | Z | | |

Astericks (*) denote the residue(s) in the peptoid sequence that contain the non-traditional functional group, in which the functional group is displayed from a backbone Carbon rather than the Nitrogen group.

Peptoid compounds of the present disclosure such as compounds of Formulas I-V, and those in Tables 1-4, can be prepared in accordance with known techniques, including but not limited to those described in: N. J. Brown, J. Johansson, and A. E. Barron, Acc. Chem. Res. 41, 1409-1417 (2008); N. P. Chongsiriwatana, J. A. Patch, A. M. Czyzewski, M. T. Dohm, A. Ivankin, D. Gidalevitz, R. N. Zuckermann, and A. E. Barron, PNAS 105, 2794-2799 (2008); K. E. Drexler, Peptide Science 96, 537-544 (2011); B. C. Gorske, B. L. Bastian, G. D. Geske, and H. E. Blackwell, J. Am. Chem. Soc. 129, 8928-8929 (2007); T. Hara, S. R. Durell, M. C. Myers, and D. H. Appella, J. Am. Chem. Soc. 128, 1995-2004 (2006); R. D. Haynes, R. J. Meagher, J.-I. Won, F. M. Bogdan, and A. E. Barron, Bioconjugate Chem. 16, 929-938 (2005); K. Kirshenbaum, A. E. Barron, R. A. Goldsmith, P. Armand, E. K. Bradley, K. T. V. Truong, K. A. Dill, F. E. Cohen, and R. N. Zuckermann, PNAS 95, 4303-4308 (1998); Y.-U. Kwon and T. Kodadek, J. Am. Chem. Soc. 129, 1508-1509 (2007); G. Maayan, M. D. Ward, and K. Kirshenbaum, PNAS 106, 13679-13684 (2009); S. M. Miller, R. J. Simon, S. Ng, R. N. Zuckermann, J. M. Kerr, and W. H. Moos, Drug Development Research 35, 20-32 (1995); P. Mora, I. Masip, N. Cortes, R. Marquina, R. Merino, J. Merino, T. Carbonell, I. Mingarro, A. Messeguer, and E. Pérez-Payá, J. Med. Chem. 48, 1265-1268 (2005); J. E. Murphy, T. Uno, J. D. Hamer, F. E. Cohen, V. Dwarki, and R. N. Zuckermann, PNAS 95, 1517-1522 (1998); K. T. Nam, S. A. Shelby, P. H. Choi, A. B. Marciel, R. Chen, L. Tan, T. K. Chu, R. A. Mesch, B.-C. Lee, M. D. Connolly, C. Kisielowski, and R. N. Zuckermann, Nature Materials 9, 454-460 (2010); J. T. Nguyen, M. Porter, M. Amoui, W. T. Miller, R. N. Zuckermann, and W. A. Lim, Chem. Biol. 7, 463-473 (2000); P. E. Nielsen, ed., Pseudo-peptides in Drug Discovery, 1st ed. (Wiley-VCH, 2004); S. H. Park and I. Szleifer, J. Phys. Chem. B 115, 10967-10975 (2011); J. A. Patch and A. E. Barron, J. Am. Chem. Soc. 125, 12092-12093 (2003); I. Peretto, R. M. Sanchez-Martin, X. Wang, J. Ellard, S. Mittoo, and M. Bradley, Chem. Commun. 2312-2313 (n.d.); M. C. Pirrung, K. Park, and L. N. Tumey, J. Comb. Chem. 4, 329-344 (2002); M. M. Reddy and T. Kodadek, Proc. Nat. Acad. Sci. USA 102, 12672-12677 (2005); M. M. Reddy, R. Wilson, J. Wilson, S. Connell, A. Gocke, L. Hynan, D. German, and T. Kodadek, Cell 144, 132-142 (2011); T. J. Sanborn, C. W. Wu, R. N. Zuckermann, and A. E. Barron, Biopolymers 63, 12-20 (2002); T. Schröder, N. Niemeier, S. Afonin, A. S. Ulrich, H. F. Krug, and S. Brase, J. Med. Chem. 51, 376-379 (2008); N. H. Shah, G. L. Butterfoss, K. Nguyen, B. Yoo, R. Bonneau, D. L. Rabenstein, and K. Kirshenbaum, J. Am. Chem. Soc. 130, 16622-16632 (2008); A. Statz, J. Kuang, C. Ren, A. Barron, I. Szleifer, and P. Messersmith, Biointerphases 4, FA22-FA32 (2009); A. R. Statz, J. P. Park, N. P. Chongsiriwatana, A. E. Barron, and P. B. Messersmith, Biofouling 24, 439-448 (2008); P. A. Wender, D. J. Mitchell, K. Pattabiraman, E. T. Pelkey, L. Steinman, and J. B. Rothbard, Proc. Nat. Acad. Sci. USA 97, 13003-13008 (2000); C. W. Wu, S. L. Seurynck, K. Y. C. Lee, and A. E. Barron, Chem. Biol. 10, 1057-1063 (2003); R. N. Zuckermann, J. M. Kerr, S. B. H. Kent, and W. H. Moos, J. Am. Chem. Soc. 114, 10646-10647 (1992); R. N. Zuckermann, E. J. Martin, D. C. Spellmeyer, G. B. Stauber, K. R. Shoemaker, J. M. Kerr, G. M. Figliozzi, D. A. Goff, and M. A. Siani, J. Med. Chem. 37, 2678-2685 (1994).

The peptoids of the present disclosure may be used to bind to, collect, purify, immobilize on a solid surface, etc., any type of antibody or antibody fragment (e.g., Fc fragments, Fab fragments, and scFV fragments), including both natural and recombinant (including chimeric) antibodies, engineered multibodies, single domain antibodies, and combinations thereof, such as divalent antibodies and camelid immunoglobulins, and both monoclonal and polyclonal antibodies, or an Fc-fusion protein. The antibodies may be of any species of origin, including mammalian (rabbit, mouse, rat, cow, goat, sheep, llama, camel, alpaca, etc), avian (e.g., chicken, turkey, etc.), shark, etc., including fragments, chimeras and combinations thereof as noted above. The antibodies may be of any type of immunoglobulin, including but not limited to IgG, IgA, IgE, IgD, IgM, IgY (avian), etc.

In some embodiments, the antibodies or Fc fragments (including fusion proteins thereof) are carried in a biological fluid such as blood or a blood fraction (e.g., blood sera, blood plasma), egg yolk and/or albumin, tissue or cell growth media, a tissue lysate or homogenate, etc.

More particularly, in some embodiments methods of binding an immunoglobulin are provided. Such methods can allow for the binding of an immunoglobulin, immunoglobulin fragment or immunoglobulin fusion protein thereof from a liquid composition containing the same. Such methods can comprise providing a solid support comprising a peptoid affinity ligand as disclosed herein, and contacting the composition to the solid support so that the immunoglobulin, immunoglobulin fragment or immunoglobulin fusion protein thereof binds to the peptoid affinity ligand of the solid support. The liquid composition can then be separated from the solid support, with the immunoglobulin, immunoglobulin fragment or immunoglobulin fusion protein thereof bound to the peptoid affinity ligand of the solid support. Additionally, the immunoglobulin, immunoglobulin fragment or immunoglobulin fusion protein thereof can be separated or eluted from the peptoid affinity ligand of the solid support. In some aspects the contacting and separating steps can be carried out continuously or in batch mode.

In some aspects the step of separating the immunoglobulin, immunoglobulin fragment or immunoglobulin fusion protein thereof from the peptoid affinity ligand is done at a pH of about 3 to about 7, preferably a pH of about 4 to about 5. For example, bound immunoglobulins or other target antigens can be released at a pH of about 3 to about 7, including for example a pH of about 4 to about 6, about 4 to about 5, about 3 to about 5 or about 4 to about 7.

The liquid composition from which the immunoglobulin or antibody is purified can comprise at least one proteolytic enzyme, and can in some aspects be a biological fluid. For example the liquid composition, sample or aliquot can comprise blood, blood sera, blood plasma, tissue or cell culture media, a cell lysate, a plant extract, or a fluid produced and/or secreted by a recombinant organism.

The methods can be carried out in like manner to those employing protein A, or by variations thereof that will be apparent to those skilled in the art. For example, the contacting and separating steps can be carried out continuously, (e.g., by column chromatography), or static (e.g., by batch mode) after which the separating step can then be carried out (e.g., by elution), in accordance with known techniques.

In some embodiments, such as when the liquid composition from which the antibodies or Fc fragments or Fc-fusion proteins are to be collected, comprises a biological fluid, the liquid composition further comprises at least one proteolytic enzyme. As discussed herein, the peptoid binding ligands are advantageously resistant to degradation by proteolytic enzymes.

In addition, photoaffinity labelling of all the above mentioned target antibodies/immunoglobulins can be carried out by replacing any of the side-chain residues of the peptoid with a photoreactive group, such as a benzophenone group.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Solid-Phase Synthesis and Purification of Peptoid and/or Peptidomimentic Ligands for the Purification of Polyclonal or Monoclonal Antibodies Peptoid affinity ligands, and/peptidomimetic ligands, were produced using a Biotage Alstra automated peptide synthesizer under microwave assistance, using previously described methods (Fara et al. Tet. Lett. 2006 47, 1011-1014; Olivos et al. Org. Lett. 2002, 4(23), 4057-4059). The ligands were synthesized on polystyrene-based resins for solid phase peptide synthesis (SPPS), including cysteamine 2-chlorotrityl resin. Prior to synthesis, the resin were swollen at 70° C. in DMF for 20 minutes. Residues added as FMOC-protect amino acid monomers were couple to the support using 5 equivalents of amino acid, HBTU, and HOBT and 10 equivalents of DIEA. Each coupling was performed in DMF at room temperature for 60 minutes. For FMOC-citruliine, the coupling was repeated with an additional 5 equivalents of amino acid prior to deprotection. The Fmoc-deprotection was accomplished with treatment of the resin with 20% piperidine in DMF at room temperature twice. The other residues of the ligand were added via conventional sub-monomer approach. First, chloroacetic acid was coupled using DIC in DMF at 40° C. for 15 minutes. Then, the appropriate primary amine is added via nucleophilic displacement of the terminal chloride in DMF at 60° C. for 30 minutes. The amines and corresponding R-groups used in the ligand synthesis are defined in Table 1. The structures of peptoids prepared and tested are defined in Table 2, 3 and 4.

The peptoids were cleaved from the synthesis resin using a mixture of trifluoroacetic acid, phenol, water, and triisopropylsilane (92.5/2.5/2.5/2.5). The crude peptoid was precipitated in ether, and then purified with low pressure reverse phase chromatography (C18, 10%-100% Acetonitrile/Water gradient with 0.1% acetic acid). The purified peptoid was lyophilized to a dry powder, and the mass of the product was confirmed with LC/MS.

When needed, protected diamines were used to allow the peptoid to be further functionalized after synthesis of the backbone sequence. Orthogonal protecting groups were chosen to survive the conditions of the peptoid synthesis, but deprotect during cleavage of the completed peptoid backbone from the synthesis resin. These amines were then converted after the cleavage of the peptoid from the resin. Conversion of the primary amine to an ureido group were accomplished by dissolving peptoid at 50 mg/mL in glacial acetic acid with 10 equivalents of potassium isocyanate, and incubating at 60° C. for 2 hours). Conversion of these amines to guanidinyl groups were accomplished after the ligands were conjugated to the chromatographic resin. Addition of uriedo group was confirmed via LC/MS.

Example 2

Conjugation of Peptoid Affinity Ligands to Chromatographic Supports

The affinity adsorbents for antibody purification were prepared by conjugating the peptoids to a chromatographic support. The peptoids were conjugated to chromatographic resins, such as Toyopearl amino AF-650-M, Sepharose or Agarose activated with pendant epoxy, bromoacetyl, tresyl, or bromohydrin groups. The peptoid was dissolved in ethanol at 30 mg/mL, and then 0.02 mmole of peptoid ligand was added to 1 mL of activated resin suspended in an equivalent volume of 0.2 M $K_2CO_3$ at pH 10. The suspension was agitated with end-over-end motion overnight at room temperature. The resin was then filtered and washed with methanol, 0.1 M glycine at pH 2.5, and then PBS. The collected supernatants and wash fractions were spectrophotometrically analyzed at 280 or 260 nm to determine the degree of conjugation relative to the initial amount peptoid in solution. The resins were then transferred and stored as 50 v/v % slurries in PBS with 0.05% sodium azide.

Following peptoid conjugation to the resin, the primary amino-group of the third residue was convert to a guanidinyl group for selected ligands (FIG. 1). The resin was suspended in pH 9 0.2 M $K_2CO_3$ buffer and then equivalents of 1H-pyrazole-1-carboxamidine hydrochloride was added. The suspension was agitated for 3 hours at 60° C. After incubation, the resin was sequentially washed with PBS, and then stored in PBS w/0.05% sodium azide as a 50 v/v % slurry.

Example 3

Affinity for Polyclonal Human IgG for Peptoid Affinity Resins

The affinity for the peptoid-resin combinations was determined by measuring the adsorption isotherm of each resin against polyclonal human IgG (Pakimna et al., J Applied Sci., 12(11): 1136-1141, 2012). Briefly, 0.050 mL of 50% resin slurry was pipetted into 6 individual wells of a 96-well filter plate (0.45 micron, PVDF, Harvard Apparatus). The resin was washed with 2×250 μL PBS using a vacuum manifold. To an individual well, 0.25 mL of a human polyclonal IgG solution at different concentrations (10, 5, 2.5, 1.25, 0.625, and 0.3125 mg/mL) was added. The resin/IgG suspension was agitated gently on a rocking table for 30 minutes. The fluid was then collected via vacuum, and the resin was washed with 0.25 mL of PBS. The filtrate and wash were then analyzed by the BCA assay to determine the residual IgG concentration relative to the starting concentration of the solution.

The equilibrium concentrations were then used to determine the capacity of the resin at each IgG concentration using the following formula:

$$q = \text{Volume}_{sample} \times (\text{Initial Concentration} - \text{Equilibrium Concentration})/\text{Volume}_{resin}$$

A plot of q versus equilibrium concentration was generated and the data fit with a hyperbola to determine the affinity constant ($K_d$) and the maximum capacity ($q_{max}$) according to the below formula, where C=the equilibrium concentration of antibody in solution:

$$q = q_{max} \times C/(k_d + C)$$

Figure 2:
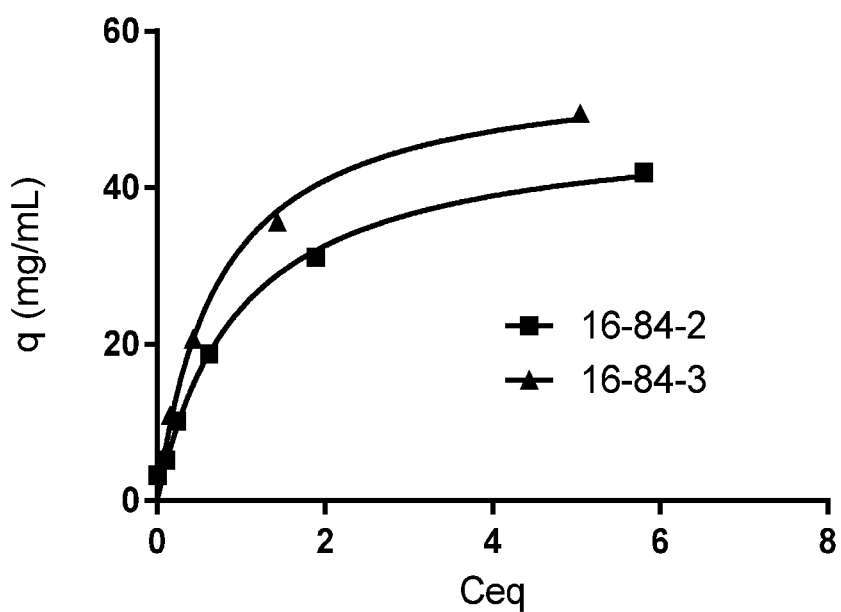
FIG. 2 is an adsorption isotherm of polyclonal human IgG, dissolved in a solution of PBS, binding to a chromatographic resin with a peptoid ligand conjugated to its surface.

Typical adsorption isotherm is shown in FIG. 2. Tabulated $K_d$ and $q_{max}$ data is found in Table 2.

Example 4

Selectivity of Peptoid Affinity Resins for IgG from Normal Rabbit Sera

Figure 3:
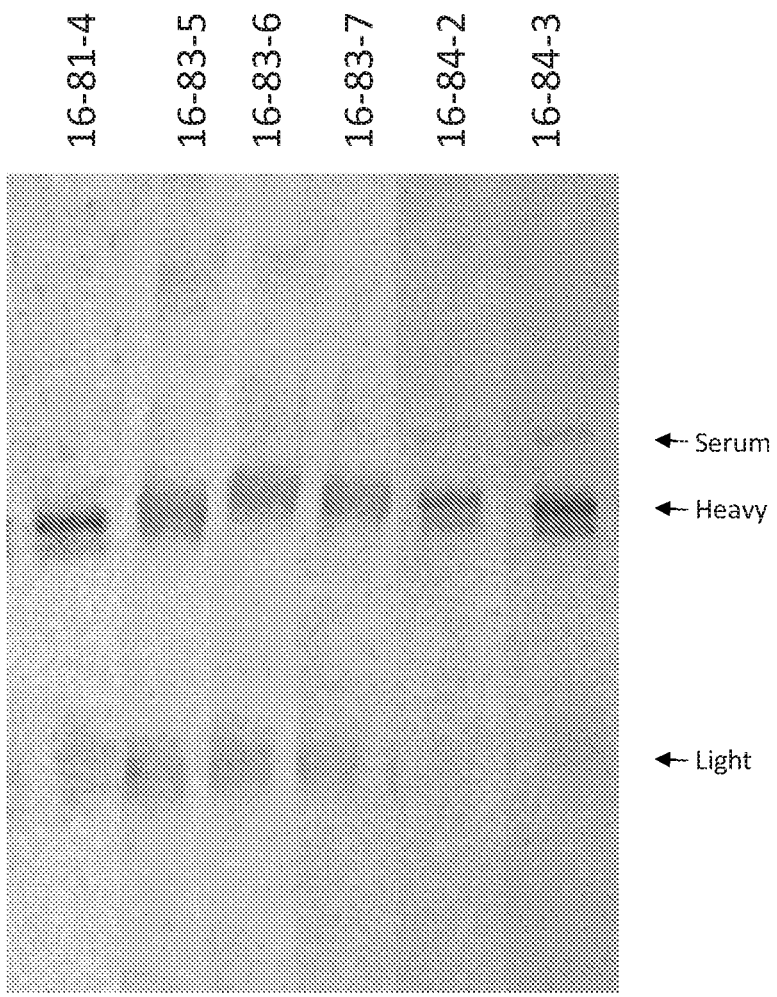
FIG. 3 is an image of a Coomassie stained SDS-PAGE analysis of pH 4.0 elutions of rabbit antibodies purified from normal rabbit serum using peptoid affinity resins.

In a 96-well filter plate (PVDF, 0.45 micron filter), 0.025 mL of resin was dispensed into each well as a 50% slurry in PBS. The resins was washed with 0.25 mL of PBS, 0.25 mL of 0.1 M glycine (pH 2.5), and then 2×0.25 mL of PBS. Unfiltered rabbit sera (0.2 mL) was then diluted with 0.05 mL of 50 mg/mL sodium caprylate dissolved in PBS. The resin wash then treated with 0.25 mL of the dilute sera. The plate was seal with a plastic adhesive film, vortexed, and then rocked for 30 minutes. The sera wash filtered from the resin, and the resin was then washed with 3×0.25 mL of a 10 mg/mL sodium caprylate solution dissolved in PBS. The antibody was then eluted with 0.25 mL of 0.1 M sodium acetate buffer at pH 4.0. The elution was then analyzed for purity by reducing SDS-PAGE gels stained with Coomassie dye (FIG. 3.)

Example 5

Selectivity of Peptoid Affinity Resins for IgA

Fifty milligrams of resins 18-59 and PV-19-1B were added to spin columns and equilibrated with 18 CV of (10 mg/mL adipic acid/0.8M NaCl pH 5.8). Sample loads of 10.0 mg human IgA per ml of resin, were loaded in the presence of CHO Conditioning media. The unbound proteins were washed from the column by using 18 CV of equilibration/wash buffer. Product elution (elute) was carried out by using 18 CV of 0.1 M Na Acetate, pH 4.0.

Figure 4A:
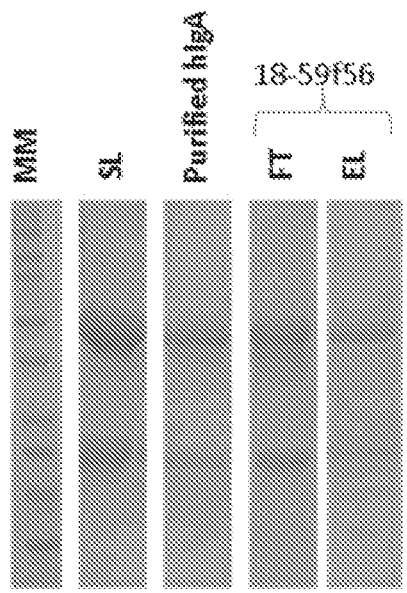
FIGS. 4A and 4B illustrate the binding affinity and yield of peptoids disclosed herein against IgA, with FIG. 4A being an image of a SDS-PAGE analysis, and FIG. 4B being a histogram of enzyme linked immunosorbent assay (ELISA) results of the yield of purified IgA, (light gray bars represent flow-through; black bars represent elute)
Figure 4B:
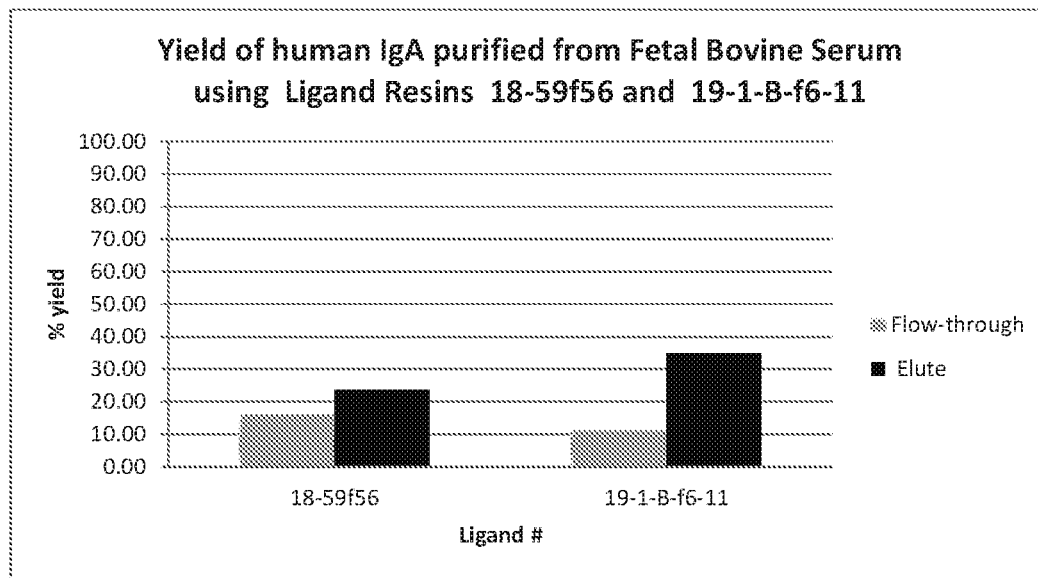

Results are shown in FIGS. 4A and 4B. FIG. 4A shows SDS-PAGE (reducing conditions) of flow-through and elution fractions. Labels: MM—molecular weight marker; SL—Sample Load; FT—Flow-through fraction; EL—Elution fraction. FIG. 4B shows results of an ELISA of flow-through and elution fractions. The amount of IgA in the collected fractions was quantified by Human IgA ELISA Quantification kit. The yield of IgA was calculated as the ratio of IgA eluted to the total IgA loaded. Labels: FT—Flow-through fraction; EL—Elution fraction.

Example 6

Selectivity of Peptoid Affinity Resins for IgM

Fifty milligrams of the resins 18-59 and PV-19-1B were added to spin columns and equilibrated with 18 CV of (10 mg/mL adipic acid/0.8M NaCl pH 5.8). Sample loads of 10.0 mg of human IgM per ml of resin, were loaded in the presence of CHO Cell Conditioning Media. The unbound proteins were washed from the column by using 18 CV of equilibration/wash buffer. Product elution (elute) was carried out by using 12 CV of 0.1 M Na Acetate, pH 4.0.

Figure 5A:
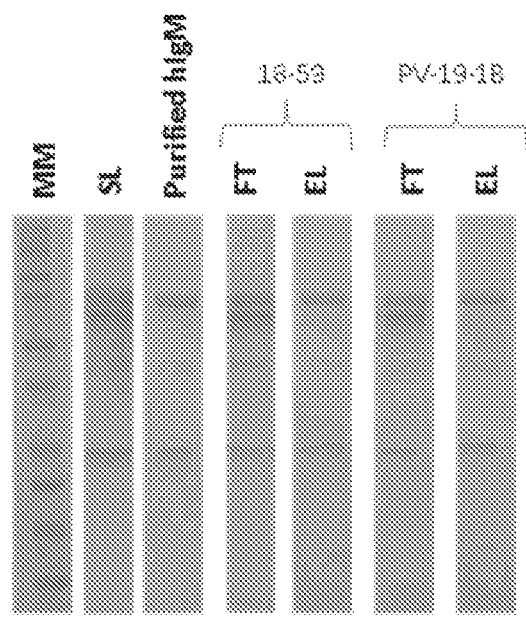
FIGS. 5A and 5B illustrate the binding affinity and yield of peptoids disclosed herein against IgM, with FIG. 5A being an image of a SDS-PAGE analysis, and FIG. 5B being a histogram of ELISA results of the yield of purified IgM, (open bars represent flow-through; closed bars represent elute)
Figure 5B:
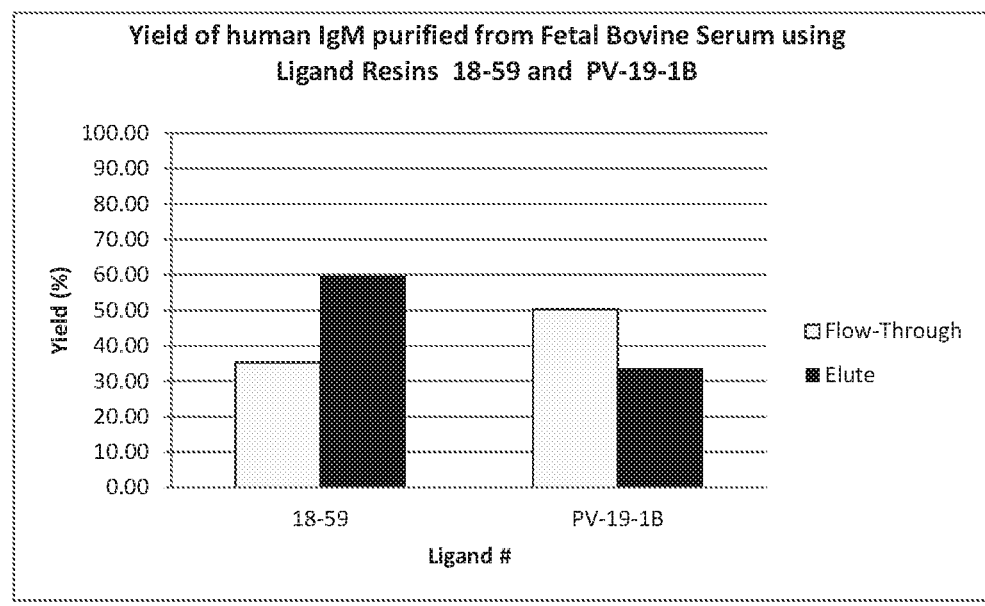

Results are shown in FIGS. 5A and 5B. FIG. 5A shows SDS-PAGE (reducing conditions) of flow-through and elution fractions. Labels: MM—molecular weight marker; SL—Sample Load; FT—Flow-through fraction; EL—Elution fraction. FIG. 5B shows results of an ELISA of flow-through and elution fractions. The amount of IgM in the collected fractions was quantified by Human IgM ELISA Quantification kit. The yield of IgM was calculated as the ratio of IgM eluted to the total IgM loaded. Labels: FT—Flow-through fraction; EL—Elution fraction.

Example 7

Selectivity of Peptoid Affinity Resins for IgY

Fifty milligrams of the ligand resins 18-59 and PV-19-1B were added to spin columns and equilibrated with 18 CV of (10 mg/mL adipic acid/0.8M NaCl pH 5.8). Sample loads of 20.0 mg of Chicken IgY, were loaded in the presence of CHO Serum Free media. The unbound proteins were washed from the column by using 18 CV of equilibration/wash buffer. Product elution (elute) was carried out by using 18 CV of 0.1 M Na Acetate, pH 4.0.

Figure 6A:
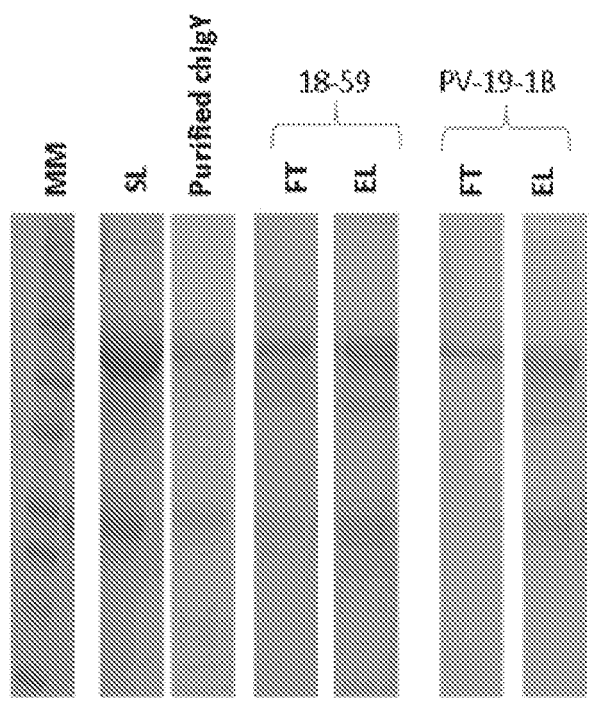
FIGS. 6A and 6B illustrate the binding affinity and yield of peptoids disclosed herein against IgY, with FIG. 6A being an image of a SDS-PAGE analysis, and FIG. 6B being a histogram of ELISA results of the yield of purified IgY, (open bars represent flow-through; closed bars represent elute).
Figure 6B:
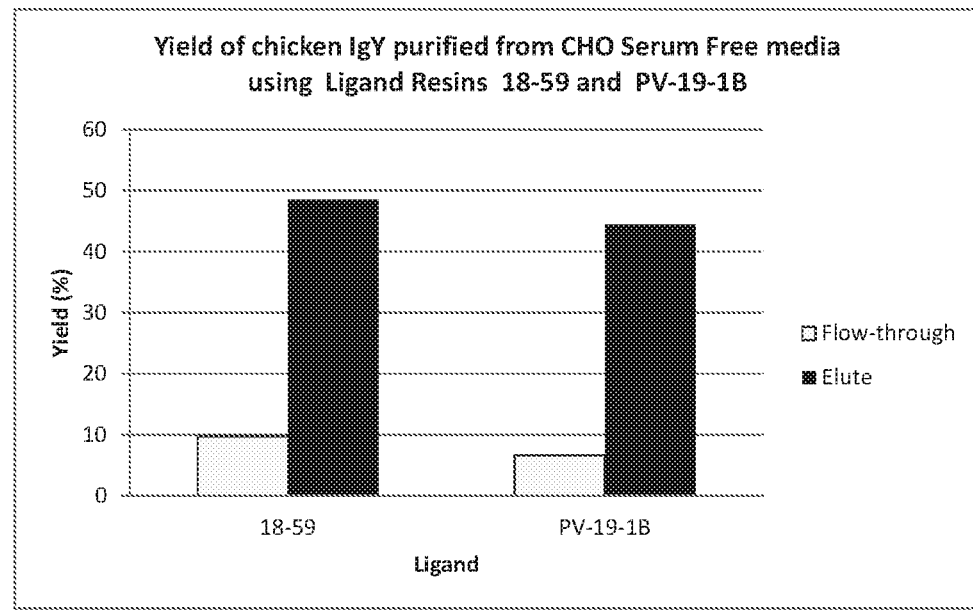

Results are shown in FIGS. 6A and 6B. FIG. 6A shows SDS-PAGE (reducing conditions) of flow-through and elution fractions. Labels: MM—molecular weight marker; SL—Sample Load; FT—Flow-through fraction; EL—Elution fraction. FIG. 6B shows results of an ELISA of flow-through and elution fractions. The amount of chicken IgY in the collected fractions was quantified by chicken IgY ELISA Quantification kit. The yield of IgY was calculated as the ratio of IgY eluted to the total IgY loaded. Labels: FT—Flow-through fraction; EL—Elution fraction.

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A peptoid affinity ligand selected from the group consisting of:

33    34
16-81-4
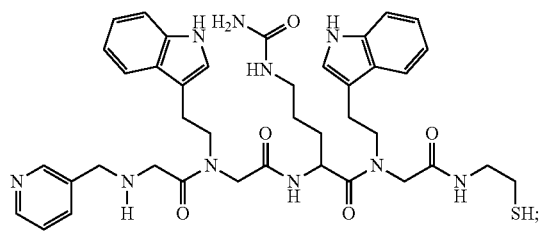
12-65-8
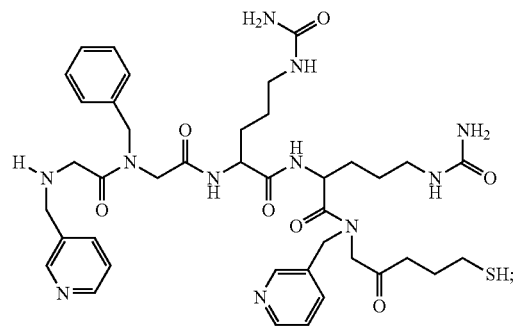
12-65-5
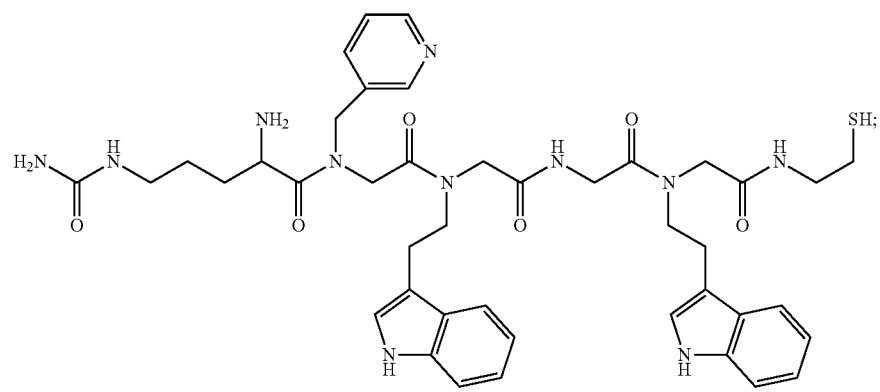
16-83-6
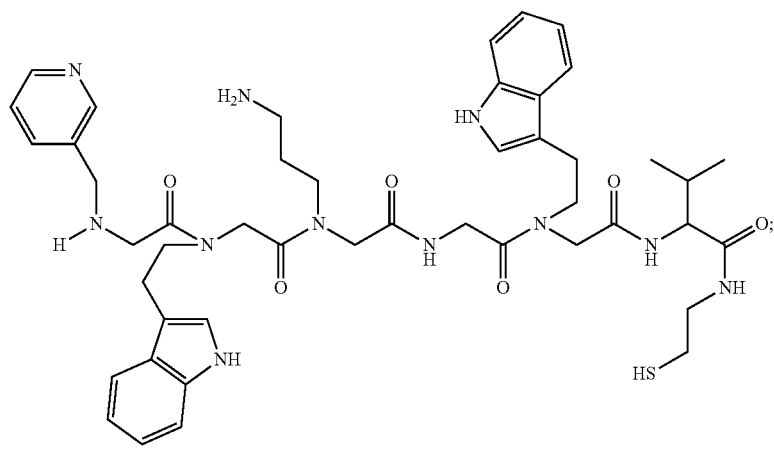
16-84-3
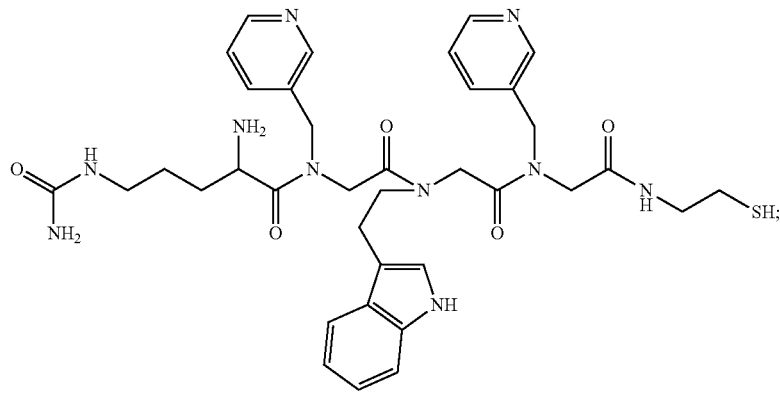

16-83-9
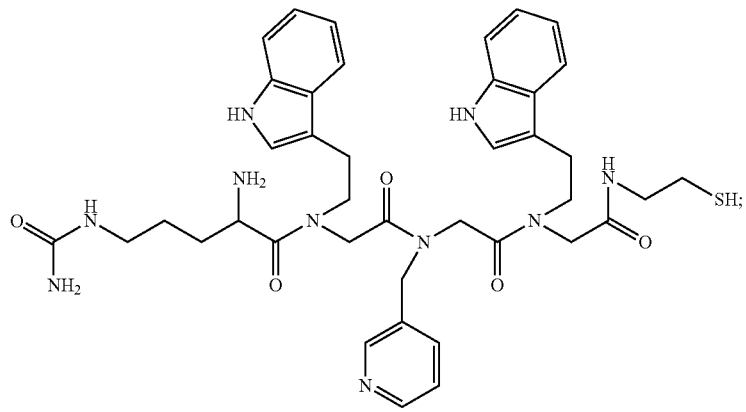
16-83-2
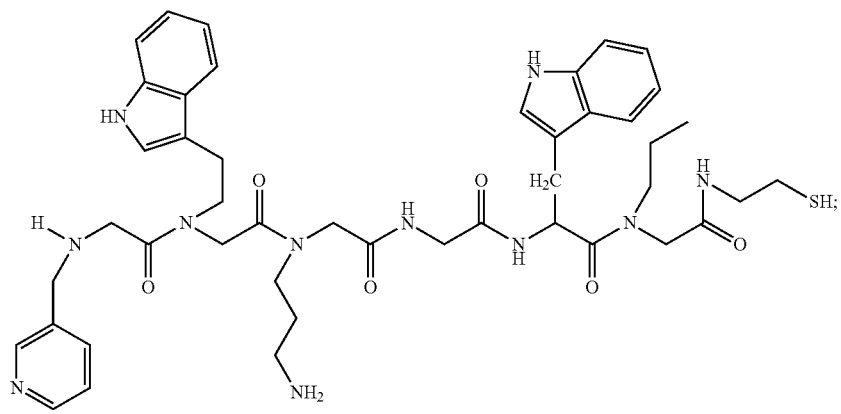
16-84-2
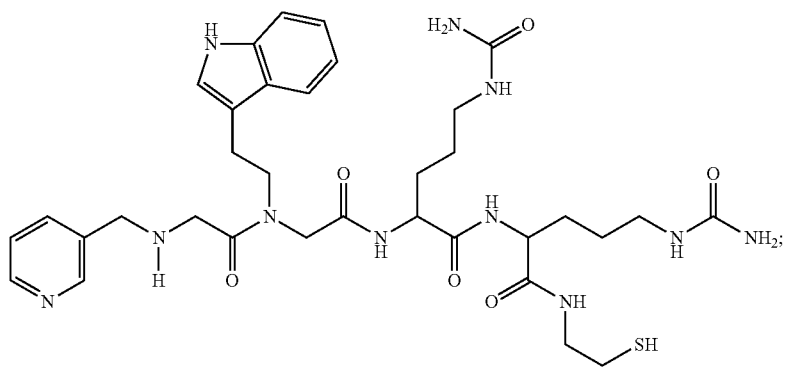
18-59
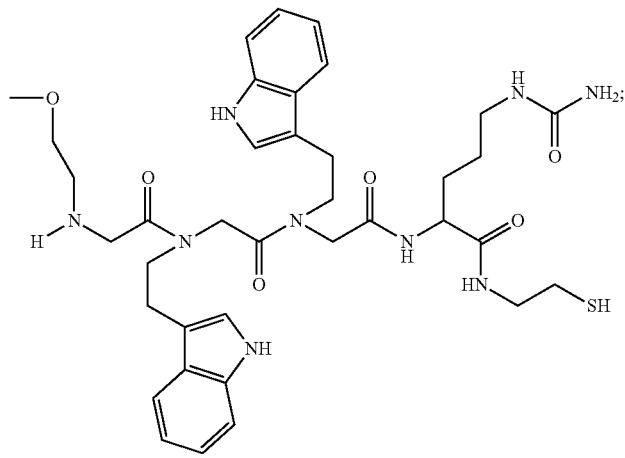

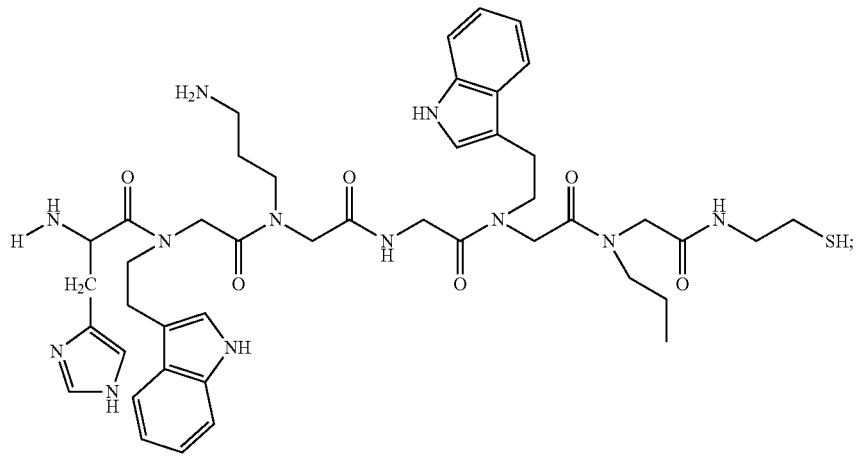
16-83-5
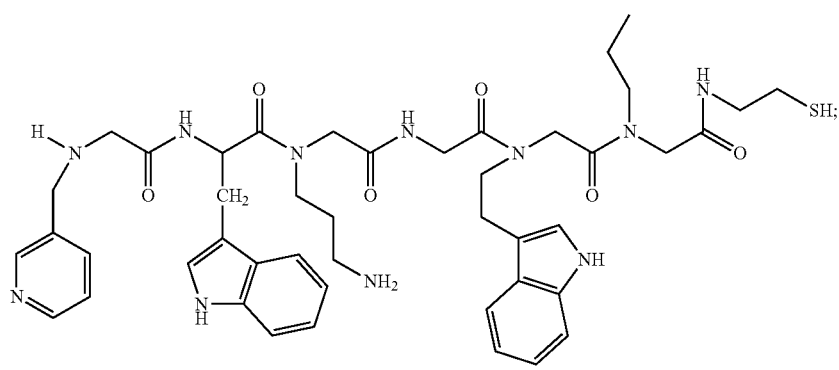
16-83-3
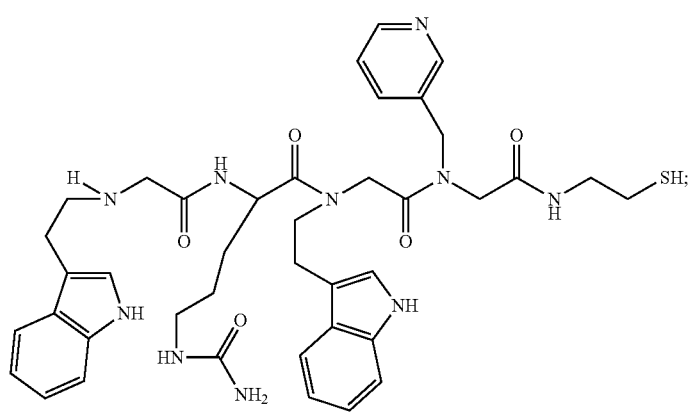
16-83-7

12-65-1
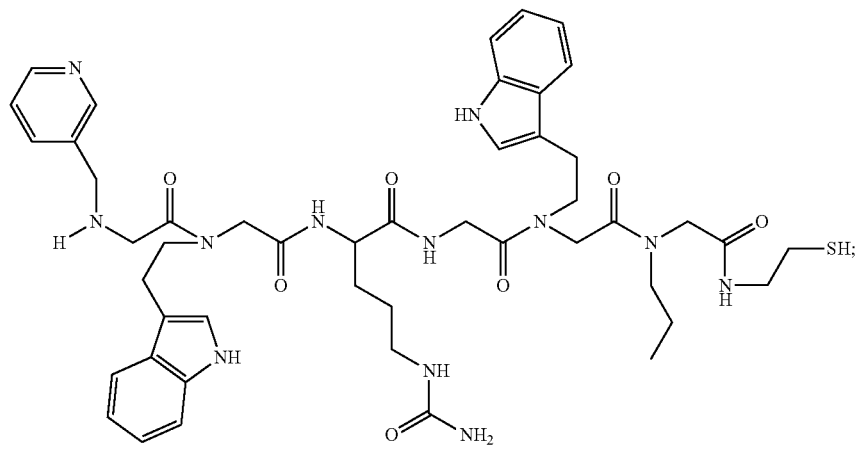
12-65-2
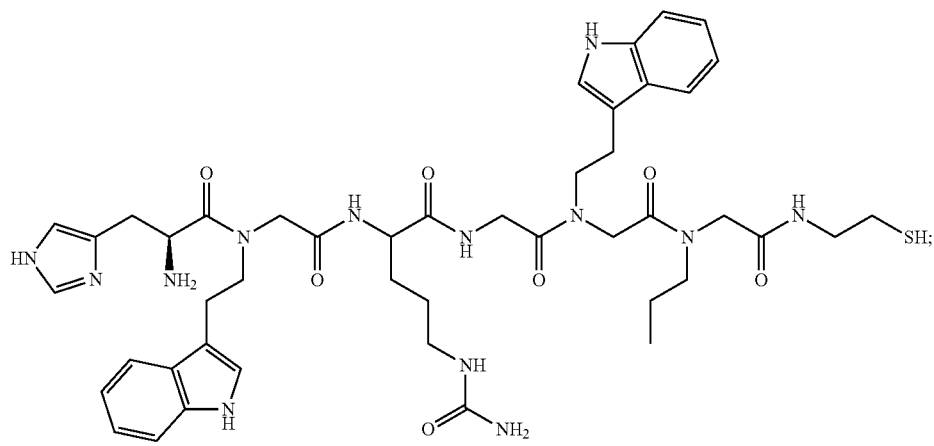
12-55-6
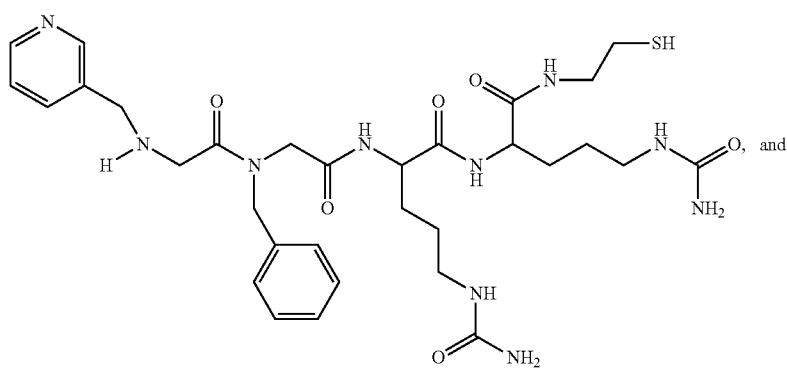

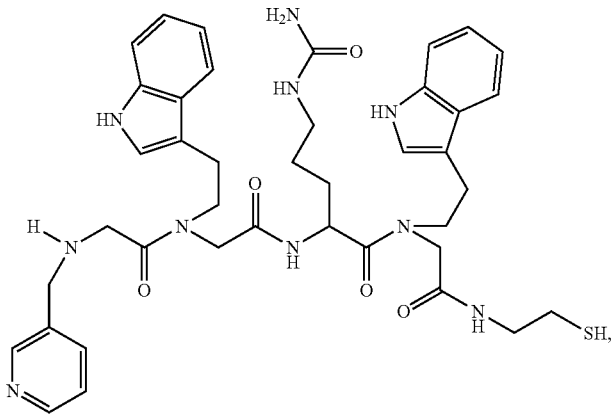

wherein the peptoid affinity ligand has a binding affinity to an immunoglobulin, immunoglobulin fragment or immunoglobulin fusion protein thereof.

2. The peptoid affinity ligand of claim 1, wherein the immunoglobulin, immunoglobulin fragment or immunoglobulin fusion protein thereof comprises IgM.

3. The peptoid affinity ligand of claim 1, wherein the immunoglobulin, immunoglobulin fragment or immunoglobulin fusion protein thereof is from a mammal, an avian or a chondrichthyes.

4. The peptoid affinity ligand of claim 1, wherein the peptoid affinity ligand is coupled to a solid support, wherein the solid support comprises a particle, an inorganic material, an organic polymer material, and/or a membrane fiber.

5. The peptoid affinity ligand of claim 1, wherein the peptoid affinity ligand is at least 50% or more resistant to proteolysis than protein-based ligands that bind immunoglobulins, wherein the peptoid affinity ligand is suitable for multiple purification cycles.

* * * * *